United States Patent
Smith et al.

(10) Patent No.: US 9,498,230 B2
(45) Date of Patent: Nov. 22, 2016

(54) MODULAR REAMING SYSTEM FOR FEMORAL REVISION

(71) Applicant: Biomet Manufacturing, LLC, Warsaw, IN (US)

(72) Inventors: Aaron P. Smith, Warsaw, IN (US); Eric J. Fontenot, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 163 days.

(21) Appl. No.: 14/100,589

(22) Filed: Dec. 9, 2013

(65) Prior Publication Data

US 2014/0100576 A1 Apr. 10, 2014

Related U.S. Application Data

(62) Division of application No. 12/502,833, filed on Jul. 14, 2009, now abandoned.

(51) Int. Cl.
*A61B 17/16* (2006.01)
*A61F 2/36* (2006.01)

(52) U.S. Cl.
CPC ........ *A61B 17/1668* (2013.01); *A61B 17/1617* (2013.01)

(58) Field of Classification Search
CPC combination set(s) only.
See application file for complete search history.

(56) References Cited

U.S. PATENT DOCUMENTS

| | | | |
|---|---|---|---|
| 5,047,035 A | 9/1991 | Mikhail et al. | |
| 5,122,146 A | 6/1992 | Chapman et al. | |
| 5,282,803 A * | 2/1994 | Lackey | A61B 17/1764 606/80 |
| 5,462,548 A * | 10/1995 | Pappas | A61B 17/1666 606/80 |
| 5,601,564 A | 2/1997 | Gustilo et al. | |
| 5,632,747 A | 5/1997 | Scarborough et al. | |
| 5,665,090 A * | 9/1997 | Rockwood | A61B 17/15 606/79 |
| 5,766,261 A | 6/1998 | Neal et al. | |
| 5,908,423 A * | 6/1999 | Kashuba | A61B 17/164 408/127 |
| 6,117,138 A | 9/2000 | Burrows et al. | |
| 6,139,551 A | 10/2000 | Michelson et al. | |
| RE37,005 E | 12/2000 | Michelson et al. | |
| 6,517,581 B2 * | 2/2003 | Blamey | A61B 17/1668 606/172 |
| 7,074,224 B2 | 7/2006 | Daniels et al. | |
| 7,632,273 B2 * | 12/2009 | Schnieders | A61B 17/1659 606/79 |
| 2004/0267267 A1 | 12/2004 | Daniels et al. | |
| 2005/0203384 A1 * | 9/2005 | Sati | A61B 6/547 600/426 |
| 2008/0161811 A1 | 7/2008 | Daniels et al. | |
| 2010/0217267 A1 * | 8/2010 | Bergin | A61F 2/3609 606/80 |

(Continued)

FOREIGN PATENT DOCUMENTS

| | | | | |
|---|---|---|---|---|
| CA | 2367520 A1 * | 7/2002 | ........... | A61B 17/164 |
| WO | WO 2007106752 A2 * | 9/2007 | ........... | A61B 17/164 |

(Continued)

*Primary Examiner* — Zade Coley
(74) *Attorney, Agent, or Firm* — Schwegman Lundberg & Woessner, P.A.

(57) ABSTRACT

A modular reaming system for reaming a plurality of pockets in an anatomical feature extends along a longitudinal axis. The system includes a first reamer in a first position on the longitudinal axis, and the first reamer reams a first pocket in the anatomical feature. The system further includes a second reamer that is removably coupled to the first reamer in a second position on the longitudinal axis. The second reamer reams a second pocket in the anatomical feature. The second reamer is keyed against rotation relative to the first reamer to ream the first and second pockets substantially simultaneously.

21 Claims, 6 Drawing Sheets

(56) References Cited

U.S. PATENT DOCUMENTS

2010/0262146 A1 10/2010 Tulkis
2011/0112540 A1* 5/2011 McLean ............... A61B 17/164
                                                        606/80

FOREIGN PATENT DOCUMENTS

| WO | WO-2007106752 A2 | 9/2007 | |
| WO | WO 2009046121 A2 * | 4/2009 | ........... A61F 2/3609 |

* cited by examiner

MODULAR REAMING SYSTEM FOR FEMORAL REVISION

CROSS REFERENCE TO RELATED APPLICATIONS

This application is a divisional of U.S. patent application Ser. No. 12/502,833 filed on Jul. 14, 2009. The entire disclosure of the above application is incorporated herein by reference.

FIELD

The following relates to a reaming tool and, more specifically, relates to a modular reaming system for a femoral revision procedure.

BACKGROUND

The statements in this section merely provide background information related to the present disclosure and may not constitute prior art.

Prosthetic joints can reduce pain due to arthritis, deterioration, deformation, and the like. Prosthetic hip joints often include a femoral component that is fixed to the patient's femur and an acetabular cup that is fixed within the patient's pelvis. More specifically, the femoral component can include a stem that extends into the patient's resected femur and a rounded head that is received within the acetabular cup. The head can articulate within the cup so as to moveably couple the femoral component within the acetabular cup.

Typically, a superior portion of the femur is partially reamed to create a reamed opening that receives the femoral component of the prosthetic hip joint. In some cases, multiple reamers of varying widths are used at different portions of the femur such that the resultant reamed opening varies in width and to match the geometry of the femoral component of the prosthetic joint. As such, the reaming process ensures that the femoral component properly fits within and fixes to the femur.

Although reaming systems have been adequate for their intended purposes, these systems can be improved. For instance, reaming processes can be time consuming and inconvenient, especially if multiple reamers are needed for reaming different portions of the femur.

SUMMARY

A modular reaming system is disclosed for reaming a plurality of pockets in an anatomical feature. The system extends along a longitudinal axis. The system also includes a first reamer in a first position on the longitudinal axis, and the first reamer reams a first pocket in the anatomical feature. The system further includes a second reamer that is removably coupled to the first reamer in a second position on the longitudinal axis. The second reamer reams a second pocket in the anatomical feature. The second reamer is keyed against rotation relative to the first reamer to ream the first and second pockets substantially simultaneously.

In another aspect, a modular reaming system is disclosed that includes a first drive coupler, a second drive coupler, and a first reamer driven in rotation by the first drive coupler. The system also includes a second reamer driven in rotation by the second drive coupler or driven in rotation by the first drive coupler.

In addition, a method of reaming a femur is disclosed that includes removably coupling a proximal reamer to a shaft fixed to a distal reamer. The method further includes retaining the proximal reamer against rotation relative to the distal reamer. Also, the method includes rotating the shaft in a single direction to substantially simultaneously ream a proximal pocket in the femur with the proximal reamer and a distal pocket in the femur with the distal reamer.

Moreover, a reaming system is disclosed that reams a femur for implantation of a femoral component of a prosthetic joint. The reaming system includes a distal member extending along a longitudinal axis. The distal member includes a first shaft, a distal reamer, and a first drive coupler. The distal reamer and the first drive coupler are fixed to opposite ends of the first shaft. The distal reamer reams a distal pocket in the femur, and the first shaft includes a first flat surface. The system further includes a proximal member including a second shaft, a proximal reamer, and a second drive coupler. The proximal reamer and the second drive coupler are fixed to opposite ends of the second shaft. The proximal reamer reams a proximal pocket in the femur, and the second shaft includes a second flat surface. The proximal member removably receives the first drive coupler and the first shaft to removably couple the proximal and distal members. The distal reamer extends out of the proximal member, and the first flat surface mates with the second flat surface to couple the distal member and the proximal member against rotation relative to each other to ream the first and second pockets substantially simultaneously. Furthermore, the system includes a retention member that limits movement of the proximal member axially relative to the distal member.

In still another aspect, a modular reaming system for reaming a plurality of pockets in an anatomical feature is disclosed. The modular reaming system includes a longitudinal axis and a first reamer in a first position on the longitudinal axis. The first reamer reams a first pocket in the anatomical feature. The system further includes a second reamer that is removably coupled to the first reamer in a second position on the longitudinal axis. The second reamer reams a second pocket in the anatomical feature. Moreover, the system includes a means for coupling the second reamer against rotation relative to the first reamer to ream the first and second pockets substantially simultaneously.

Still further, a modular reaming system for reaming a plurality of pockets in an anatomical feature is disclosed. The modular reaming system includes a longitudinal axis and a first member with a first reamer that reams a first pocket in the anatomical feature. The first member includes a first surface. The system further includes a second member with a second reamer that reams a second pocket in the anatomical feature. The second reamer is removably coupled to the first member. The second member includes a second surface that is complementary to the first surface so that rotation of one of the first and second members about the longitudinal axis causes rotation of the other of the first and second members for substantially simultaneous formation of the first and second pockets.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. Moreover, while the reaming system described herein is described in relation to reaming an intramedullary (IM) canal of a femur, the reaming system can be used in any other area of a patient as well.

Figures 1, 2:
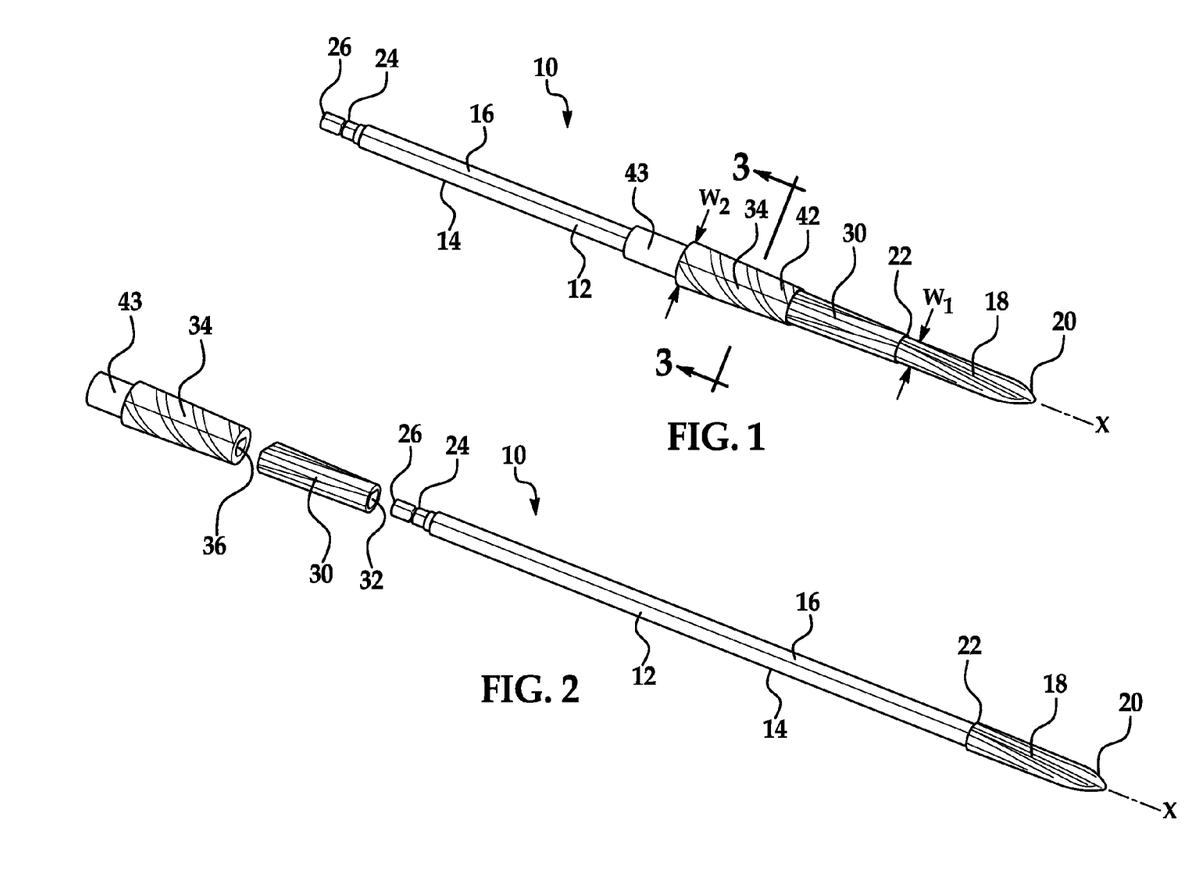
FIG. 1 is an isometric view of an exemplary embodiment of a reaming system according to various teachings of the present disclosure.
FIG. 2 is an exploded isometric view of the reaming system of FIG. 1.

Referring initially to FIGS. 1 and 2, a reaming system 10 is illustrated according to various exemplary embodiments of the present disclosure. The reaming system 10 can include a shaft 12. The shaft 12 can be elongate and can have a substantially straight longitudinal axis X. Furthermore, the shaft 12 can have a rounded portion 14 and a flat surface 16 as shown in the sectional view of FIG. 3. More specifically, the shaft 12 can be partially circular in cross section due to the rounded portion 14, and the flat surface 16 can be included on a chord of the cross section. The rounded portion 14 and the flat surface 16 can both extend along the majority of the shaft 12 in a direction substantially parallel to the longitudinal axis X. Also, the flat surface 16 can be located on only a portion of the shaft 12.

The system 10 can also include a first reamer 18. The first reamer 18 can be disposed at a first (distal) end 20 of the shaft 12. The first reamer 18 can be substantially cylindrical with a pointed end and can be fluted so as to perform reaming operations, for instance, in bone or other suitable materials. The first reamer 18 can be fluted in either the left-hand or right-hand direction about the axis X. In some embodiments, the first reamer 18 is integrally coupled to the shaft 12 so as to be monolithic; however, the first reamer 18 can be removably coupled to the shaft 12 in some embodiments. The shaft 12 can also include a shoulder 22 adjacent the first reamer 18. As shown, the shoulder 22 can be generally wider than surrounding portions of the shaft 12.

Figure 5:
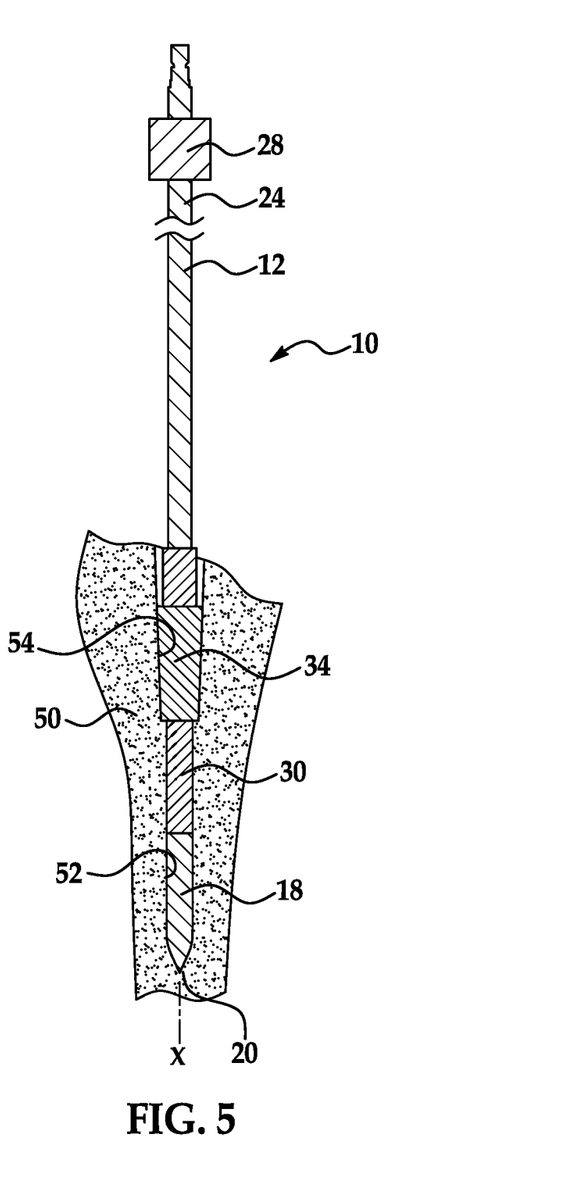
FIG. 5 is a sectional view of the reaming system of FIG. 1 shown during a reaming procedure.

The shaft 12 can also include a first drive coupler 24. The first drive coupler 24 can be coupled to the shaft 12 at a second (proximal) end 26 thereof. The drive coupler 24 can include any suitable features for removably coupling the shaft 12 to a driving device 28 (FIG. 5). The driving device 28 can be a motor powered by electricity, pneumatics, hydraulics, etc. The driving device 28 can also be powered by manual input. As such, the driving device 28 can drivingly rotate the shaft 12 about the axis X.

As shown in FIGS. 1 and 2, the system 10 can further include one or more modular spacers 30. Each spacer 30 can be tubular in shape and can have a width (i.e., diameter) substantially equal to that of the first reamer 18. The spacer 30 can include grooves so that, during reaming operation, materials removed by the first reamer 18 can move along the axis X and pass the spacer 30. The spacer 30 can also include an aperture 32, such as a through-hole that extends therethrough. In the embodiment shown, the aperture 32 can slidably receive the second end 26 of the shaft 12 and can slide generally parallel to the axis X on the shaft 12. As will be described, the aperture 32 can be shaped so as to be keyed against rotation about the axis X relative to the shaft 12. As the spacer 30 slides toward the first reamer 18, the spacer can eventually abut the shoulder 22 of the shaft 12. As such, the shoulder 22 can limit movement of the spacer 30 along the axis X in a direction generally toward the first reamer 18. The system 10 can also include a separate retention member, such as a biased detent pin or other quick-connect coupling (not shown), that limits movement of spacer 30 along the axis X in a direction generally away from the first reamer 18. As will be described, the spacer 30 maintains the first reamer 18 a predetermined distance away from other components of the system 10, and this predetermined distance can be varied on a patient-by-patient basis by interchanging the spacer 30 with another.

Figure 3:
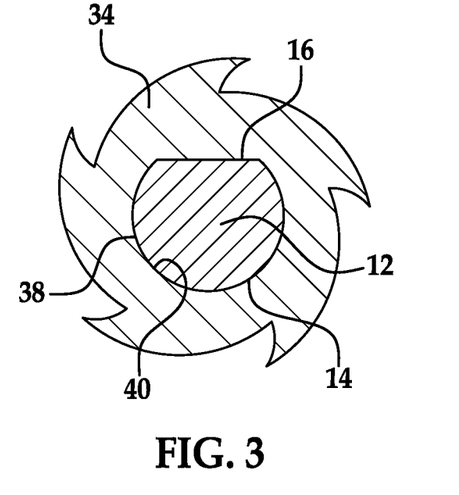
FIG. 3 is a sectional view of the reaming system taken along the line 3-3 of FIG. 1.

Furthermore, the system 10 can additionally include a second reamer 34. The second reamer 34 can be generally tubular in shape and can be fluted in order to remove and reduce material during reaming operations. The second reamer 34 can be fluted in either the left-hand or right-hand direction about the axis X; however, it will be appreciated that the second reamer 34 is fluted in the same direction as the first reamer 18. Also, the second reamer 34 can include an aperture 36, such as a through-hole, that extends therethrough. The aperture 36 can include a rounded portion 40 and a flat surface 38 as shown in FIG. 3. The aperture 36 can slidably receive the shaft 12 in order to couple the second reamer 34 to the shaft 12. More specifically, the flat surface 38 of the second reamer 34 can mate with the flat surface 16 of the shaft 12, and the rounded portion 40 of the second reamer 34 can mate with the rounded portion 14 of the shaft 12 such that the second reamer 34 continuously extends about and surrounds the shaft 12 as shown in FIG. 3. Accordingly, the second reamer 34 can be substantially locked against rotation about the axis X (i.e., keyed to the shaft 12). However, it will be appreciated that the reaming system 10 can include any suitable anti-rotation component for coupling the second reamer 34 against rotation relative to the axis X of the shaft 12. It will also be appreciated that the spacer 30 can be similarly locked against rotation relative to the shaft 12.

The second reamer 34 can slide from the second end 26 generally parallel to the axis X toward the spacer 30 and the first reamer 18. Also, the second reamer 34 can abut against the spacer 30 such that the spacer 30 limits movement of the second reamer 34 and maintains a predetermined amount of space between the first and second reamers 18, 34. The system 10 can also include a separate retention member, such as a biased detent pin or other quick-connect coupling (not shown), that limits movement of spacer 30 along the axis X in a direction generally away from the first reamer 18.

Furthermore, in some embodiments, the system 10 can be used without the spacer 30 such that the second reamer 34 abuts directly against the shoulder 22 when coupled to the shaft 12. Moreover, in some embodiments, the system 10 can include a plurality of second reamers 34 and/or a plurality of spacers 30, which are each coupled to the shaft 12 at a respective location along the axis X.

As shown in FIG. 1, the first reamer 18 can have a maximum width $W_1$ (diameter) that is less than a maximum width $W_2$ (diameter) of the second reamer 34. More specifically, the first reamer 18 can be at least partially tapered and can have a maximum width $W_1$ adjacent the shoulder 22. Likewise, the second reamer 34 can include a tapered portion 42 and an axially straight portion 43. The second reamer 34 can have a maximum width $W_2$ at the intersection between the tapered portion 42 and the axially straight portion 43. As will be discussed, the different widths $W_1$, $W_2$ and lengths of the first and second reamers 18, 34 can be adapted such that the system 10 can ream pockets (e.g., bores) that substantially match the geometry of an associated prosthetic device (FIG. 10) intended for implantation.

Figure 10:
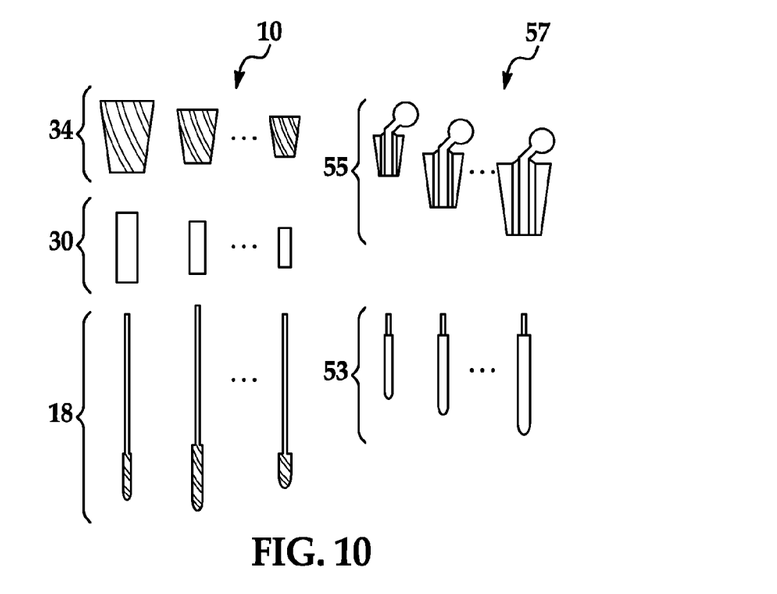
FIG. 10 is a view of a modular reaming system or kit shown in association with a corresponding modular prosthetic implant system.

It will be appreciated that when the second reamer 34 is coupled to the shaft 12, the second reamer 34 can be driven in rotation about the axis X simultaneously with the first reamer 18. More specifically, the first drive coupler 24 can be coupled to the driving device 28 (FIG. 5), and the shaft 12 can be drivingly rotated about the axis X. This, in turn, simultaneously rotates both the first and second reamers 18, 34 in the same direction about the axis X. Accordingly, as shown in FIG. 5, the first reamer 18 can be used to create a reamed distal pocket 52 (i.e., distal bore) in a femur 50 when the driving device 28 rotates the shaft 12. Also, because the second reamer 34 rotates with the first reamer 18 and because the second reamer 34 is fluted in the same direction as the first reamer 18, the second reamer 34 can simultaneously create a reamed proximal pocket 54 (i.e., proximal bore) that is in communication with the distal pocket 52 in the femur 50. It will be appreciated that the distal and proximal pockets 52, 54 can provide an intramedullary canal for a femoral portion of a prosthetic device (FIG. 10). The distal and proximal pockets 52, 54 can be concentric. The spacer 30 can maintain the predetermined distance between the first and second reamers 18, 34 and, thus, ensure that the distal and proximal pockets 52, 54 are at a predetermined distance away from each other. Accordingly, the pockets 52, 54 can be created in a convenient, accurate, and time-efficient manner.

Furthermore, as shown in FIG. 10, the system 10 can be a modular kit that includes a plurality of different first reamers 18, spacers 30, and second reamers 34. The reamers 18, 34 can vary by length, width, fluting pattern, material or in any other suitable fashion. Also, the spacers 30 can vary by length, width, material, or in any other suitable fashion. Thus, the medical professional can pick and choose from among the first reamers 18, the spacers 30, and the second reamers 34 for performing a reaming operation that substantially matches the geometry of the prosthetic that will be implanted.

Once the distal and proximal pockets 52, 54 are formed, one or more prosthetic members 53, 55 (FIG. 10) can be implanted within the femur 50. For instance, in some embodiments, a distal prosthetic member 53 can be implanted within the distal pocket 52, and a proximal prosthetic member 55 can engage the distal prosthetic member 53 and be implanted within the proximal pocket 54.

As shown in FIG. 10, the prosthetic members 53, 55 can be part of modular prosthetic system 57. The system 57 can include a plurality of distal prosthetic members 53 (i.e., stems), each having different geometries (e.g., different lengths, widths, etc.). The system 57 can further include a plurality of proximal prosthetic members 55 (i.e., bodies), each having different geometries (e.g., different lengths, widths, etc.). Each distal prosthetic member 53 can engage and fix to each of the proximal prosthetic members 55, for instance, by a Morse taper-type coupling. Thus, the surgeon can select and customize a distal prosthetic member 53 and a proximal prosthetic member 55 on a patient-by-patient basis. For instance, the system 57 can incorporate components from the commercially available ARCOS system, available from Biomet, Inc. of Warsaw, Ind.

Also, as shown in FIG. 10, the reaming system 10 can be directly associated geometrically with the modular prosthetic system 57. For instance, the system 10 can include a plurality of first reamers 18 of different geometries (e.g., different lengths, widths, etc.), and each first reamer 18 can have a geometry that substantially matches one of the distal prosthetic members 53. Likewise, the system 10 can include a plurality of second reamers 34 of different geometries, and each second reamer 34 can have a geometry that substantially matches one of the proximal prosthetic members 55. Furthermore, the system 10 can include a plurality of spacers 30 of different lengths, each corresponding to the assembled distance between the distal and proximal prosthetic members 53, 55. Thus, once the surgeon has selected the distal and proximal prosthetic members 53, 55 that will be implanted, the surgeon can use the corresponding first reamer 18, spacer 30, and second reamer 34 to ream the femur 50. Because the first reamer 18, spacer 30, and second reamer 34 match the prosthetic members 53, 55 geometrically, and because the first reamer 18, spacer 30, and second reamer 34 are engaged together during reaming, the reamed pockets 52, 54 (FIG. 5) can be very accurately formed simultaneously. As such, the system 10 ensures that the prosthetic members 53, 55 can fit securely within the femur 50.

Figure 4:
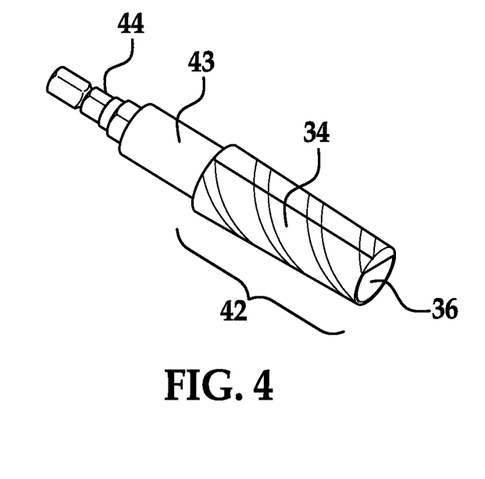
FIG. 4 is an isometric view of the reaming system of FIG. 1 in a different configuration.

Also, as shown in FIG. 4, the second reamer 34 can be alternatively and removably coupled to a second drive coupler 44. For instance, the second reamer 34 can be removably coupled to the second drive coupler 44 via a biased detent pin (not shown) or in any other suitable fashion. Also, the second drive coupler 44 can be included on a shaft that slidably receives the second reamer 34. Accordingly, the second reamer 34 can be drivingly coupled to the driving device 28 separate from the first reamer 18 when necessary. For instance, if the distal prosthetic member 53 (FIG. 10) is already inserted into the distal pocket 52 (FIG. 5), and the proximal pocket 54 needs to be widened, the second reamer 34 can be coupled to the second drive coupler 44 and drivingly attached to the driving device 28 to widen the proximal pocket 54. In some embodiments, the aperture 36 of the second reamer 34 can be wide enough such that the second reamer 34 can fit partially over and rotate relative to the distal prosthetic member 53 in order to ream out the proximal pocket 54. Thus, the surgeon conveniently has the option to create the pockets 52, 54 simultaneously or in separate steps.

Accordingly, the system 10 allows the medical professional to ream pockets 52, 54 within a femur 50 or other anatomical feature of a patient with a single modular system in one step. It will be appreciated that the reamers 18, 34 can be arranged on the shaft 12 to match the geometry of modular prosthetic members 53, 55. The reamers 18, 34 can also be used separately to ream the pockets 52, 54 in separate steps. Accordingly, the system 10 can be very convenient and time-efficient for the medical professional when reaming the femur 50 or other suitable anatomical feature. Also, the system 10 can be varied according to the patient's anatomy, according to the prosthetic members 53, 55, and the like for added convenience. Moreover, the system 10 can ream the pockets 52, 54 very accurately so that the prosthesis is more likely to properly fit within the femur 50.

Referring now to FIGS. 6, 7, 8, and 11 another exemplary embodiment of the system 110 is illustrated. Components that correspond to those of FIGS. 1-5 are indicated by corresponding reference numerals, increased by 100.

As shown, the system 110 can include a first member 160 and a second member 162. The first member 160 can include a first shaft 112 (FIG. 7) with a first reamer 118 (e.g., a distal reamer) and a first drive coupler 124 (FIG. 7) fixed at opposite ends. The second member 162 can also include a second shaft 164 with a second reamer 134 (e.g., a proximal reamer) and a second drive coupler 144 fixed at opposite ends.

Figure 6:
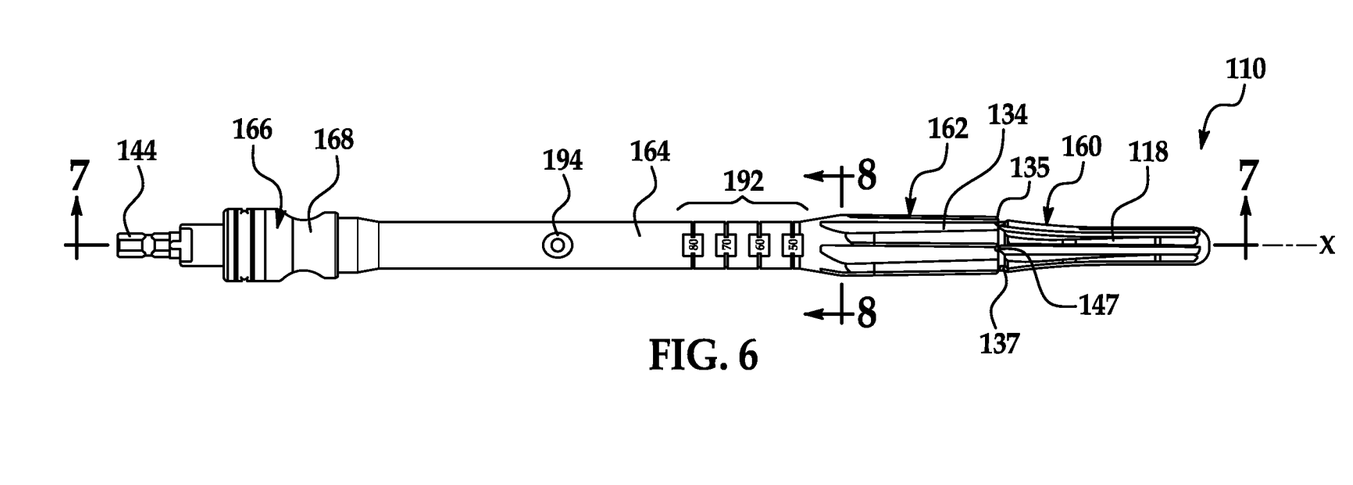
FIG. 6 is a side view of a reaming system according to another exemplary embodiment.
Figure 7:
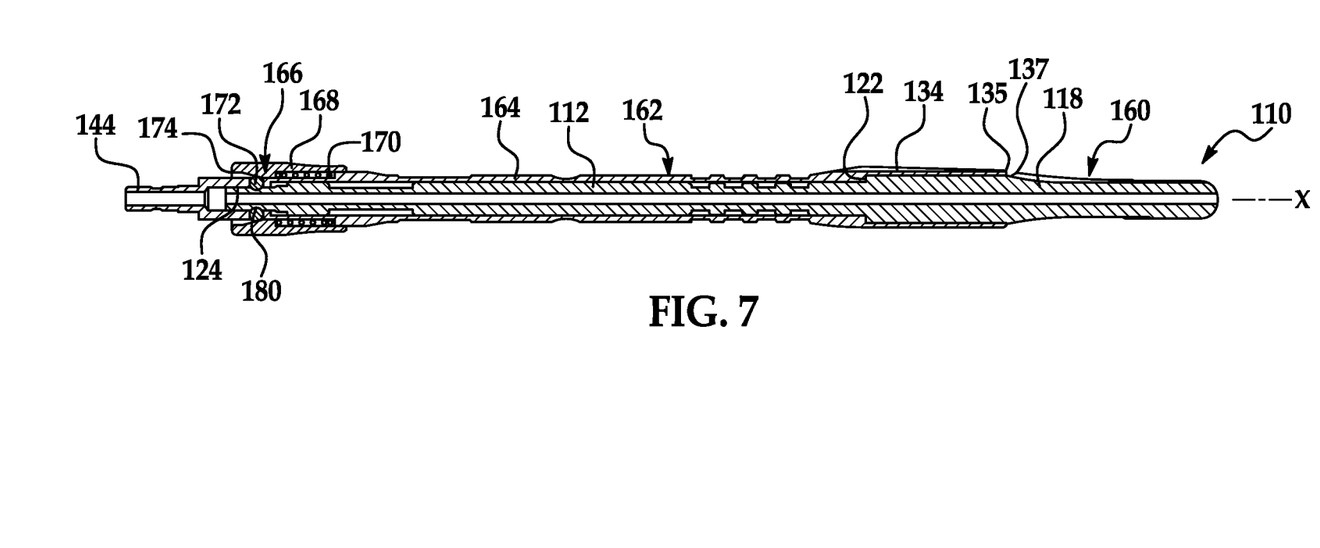
FIG. 7 is a sectional view of the reaming system taken along the line 7-7 of FIG. 6.
Figures 11, 12:
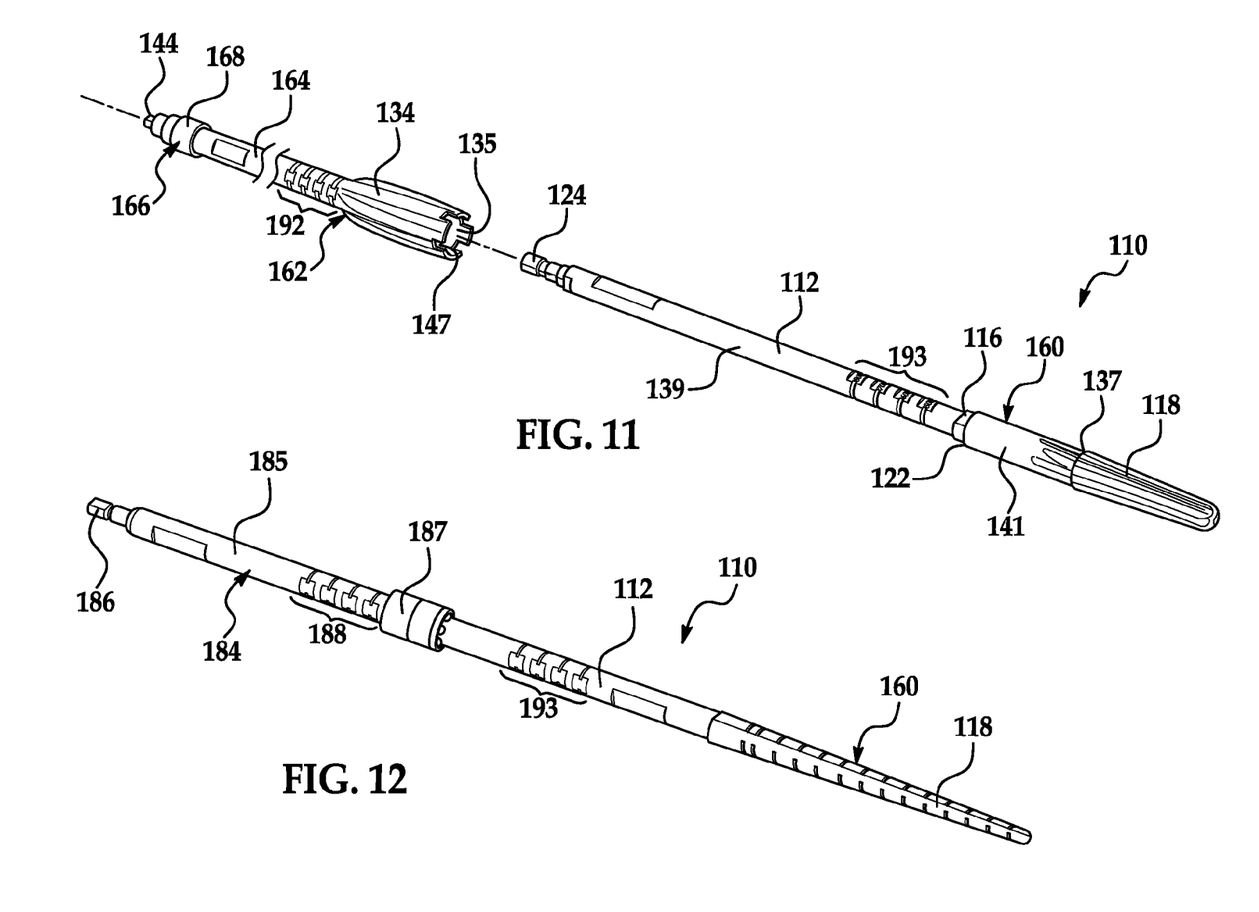
FIG. 11 is a perspective, exploded view of the reaming system of FIG. 6.
FIG. 12 is a perspective view of the reaming system of FIG. 6 shown with an extension member.

The first reamer 118 can be elongate and fluted. As shown in FIGS. 6, 7, and 11, the first reamer 118 can have a slight taper such that the width (i.e., diameter) increases along the axis X toward the first shaft 112. Moreover, the first reamer 118 can include a shoulder 137.

The first shaft 112 can be elongate and can include a first portion 139 and a second portion 141. The first and second portions 139, 141 can be substantially cylindrical, and the second portion 141 can be wider (i.e., can have a larger diameter) than the first portion 139. The second portion 141 can be disposed between the first reamer 118 and the first portion 139 of the shaft 112.

Also, the second reamer 134 can be elongate and fluted and can be tapered. The second reamer 134 can also include a leading end 135 that is beveled so as to improve reaming operations.

In some embodiments, the second member 162 can include depth indicators 192 (FIGS. 6 and 11). Likewise, the first member 112 can include depth indicators 193 (FIG. 11). The depth indicators 192, 193 can be of any suitable type, such as inscribed gradations with numbers. The depth indicators 192, 193 can be used to visually indicate the depth of the respective member 112, 162 as the member 112, 162 performs reaming operations.

The first member 160 can be removably coupled to the second member 162. For instance, the second member 162 can be hollow so as to slidably receive the first drive coupler 124 and the first shaft 112, and such that the first and second members 160, 162 are coaxial as shown in FIG. 7. As shown in FIG. 7, the first member 160 substantially fills and mates with the second member 162. When coupled, the first reamer 118 extends out from the second member 162 and is disposed at a distance axially away from the second reamer 134. Also, as shown in FIGS. 6 and 7, the leading end 135 of the second reamer 134 can be disposed directly adjacent the shoulder 137 of the first reamer 118 when the first and second members 160, 162 are coupled. The leading end 135 of the second reamer 134 can additionally include teeth 147 (FIGS. 6 and 11) that increase the cutting ability of the second reamer 134.

Figure 8:
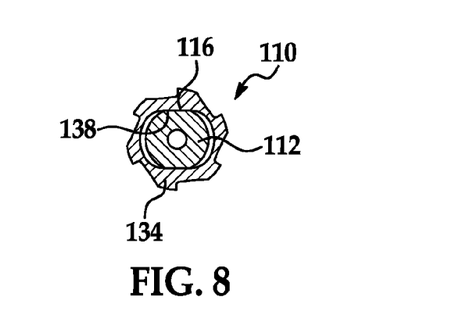
FIG. 8 is a sectional view of the reaming system taken along the line 8-8 of FIG. 6.

Also, as shown in FIGS. 8 and 11, the first shaft 112 can include a plurality of first flat surfaces 116, and as shown in FIG. 8, the second shaft 164 can include a plurality of second flat surfaces 138. For instance, as shown in FIGS. 8 and 11, the first shaft 112 can include two first flat surfaces 116 that are disposed symmetrically on opposite sides of the axis X, between the first and second portions 139, 141 of the first shaft 112. The second shaft 164 can include two corresponding second flat surfaces 138 that are disposed symmetrically on opposite sides of the axis X. The flat surfaces 116, 138 can abuttingly mate to couple the first and second members 160, 162 against rotation about the axis X relative to each other.

Moreover, the first shaft 112 can additionally include a shoulder 122 (FIGS. 7 and 11). The shoulder 122 can be included between the first and second portions 139, 141 of the first shaft 112. As shown in FIG. 7, the second member 162 can abut against the shoulder 122 to limit movement of the second reamer 134 axially toward the first reamer 118.

Furthermore, in some embodiments, the second member 162 can include a retention member 166 (FIG. 7) that limits movement of the second reamer 134 away from the first reamer 118. The retention member 166 can be a quick-connect coupling of a known type. More specifically, the retention member 166 can be operably supported on the second member 162, and the retention member 166 can include a sleeve 168, a biasing member 170, and a bearing 172 (FIG. 7). The sleeve 168 can be ring-shaped and can be slidably received on the second shaft 164 to slide axially on the second shaft 164. The biasing member 170 can be of any suitable type, such as a coiled spring and can be received on the second shaft 164. The bearing 172 can be of any suitable type, such as a plurality of ball bearings that are spaced evenly around the second shaft 164 and that are biased radially outward from the axis X. The biasing member 170 can bias the sleeve 168 toward the second drive coupler 144. Also, the sleeve 168 can include a ramp 174.

As the sleeve 168 moves away from the second reamer 134, the ramp 174 cams the bearing 172 toward the axis X and into a groove 180 formed on the first shaft 112 of the first member 160. As such, the first member 160 is limited against movement in a direction parallel to the axis X relative to the second member 162. Furthermore, as the sleeve 168 moves toward the second reamer 134, the bearing 172 is able to bias away from the axis X and out of the groove 180, thereby releasing the first member 160 from the second member 162.

Accordingly, the retention member 166 conveniently couples and de-couples the first and second members 160, 162. It will be appreciated that the retention member 166 can be used to limit movement of the second member 162 in both axial directions relative to the first member 160.

Thus, the first and second members 160, 162 can be axially and rotatably fixed, and the system 110 can be used to simultaneously ream a plurality of regions of a femur 50, similar to the embodiment of FIG. 5. It will be appreciated that a spacer 30 of the type shown in FIGS. 1-5 can be included between the first and second reamers 118, 134 to maintain a predetermined axial distance between the first and second reamers 118, 134.

Figure 9:
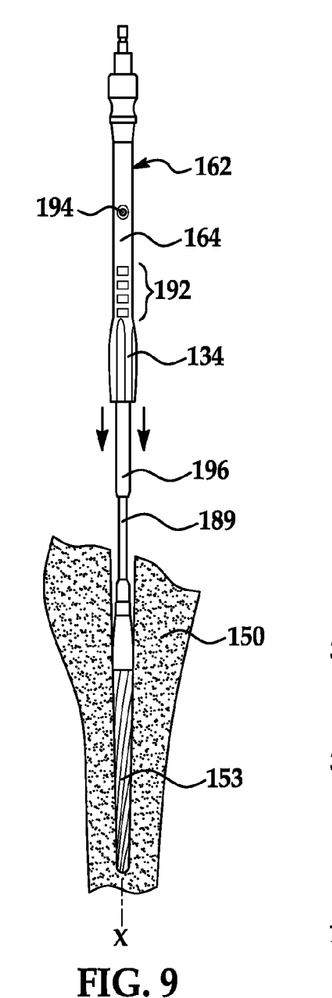
FIG. 9 is a side view of a portion of the reaming system of FIG. 6 shown during use.

Also, the first and second members 160, 162 can be used separately to individually ream corresponding portions of the femur 50 as discussed above. For instance, the first member 160 can be used separate from the second member 162 to perform distal reaming of a femur. Next, as shown in FIG. 9, the second member 162 can be used after a distal prosthetic member 153 has been implanted in the femur 150. More specifically, an alignment rod 189 can be removably coupled to the distal prosthetic member 153, and the second member 162 can slide over and receive the alignment rod 189. The alignment rod 189 ensures that the second member 162 is aligned substantially coaxially relative to the distal prosthetic member 153; however, the second member 162 remains free to move axially and rotate about the axis X relative to the alignment rod 189. Then, the second member 162 can be used to proximally ream the femur 150 and create space for implantation of the proximal prosthetic member (not shown).

Also, the second member 162 can include an opening 194, and the alignment rod 189 can include a visual indicator 196 that appears within the opening 194 when the second member 162 is at a predetermined depth within the femur 150. Accordingly, the second member 162 can ream the femur 150 very accurately, even when separate from the first member 160.

In addition, as shown in FIG. 12, the system 110 can include an extension member 184. The extension member 184 can be used for reaming with the first member 160 separate from the second member 162. The extension member 184 can be elongate and axially straight. The extension member 184 can include a shaft 185 with a third drive coupler 186 and a retention member 187 on opposite ends. The retention member 187 can be of a quick-connect type, similar to the retention member 166 described above and shown in FIGS. 6, 7, and 11. The shaft 185 can also include depth indicators 188, such as inscribed gradations with numbers.

As shown in FIG. 12, the retention member 187 can couple to the first member 160 in a manner similar to the retention member 166 described above. Also, the third drive coupler 186 can couple to a driving device 28 of the type described above and shown schematically in FIG. 5. Thus, the extension member 184 can be removably coupled to the first member to effectively extend the reach of the first member 160 during distal reaming. As such, the first member 160 can be used to ream relatively deeply within the femur 150.

It will be appreciated that the system 110 can include a plurality of extension members 184 of different axial lengths. As such, the surgeon can select an extension member 184 to perform distal reaming to a predetermined depth, corresponding to the length of the selected extension member 184.

Figure 13:
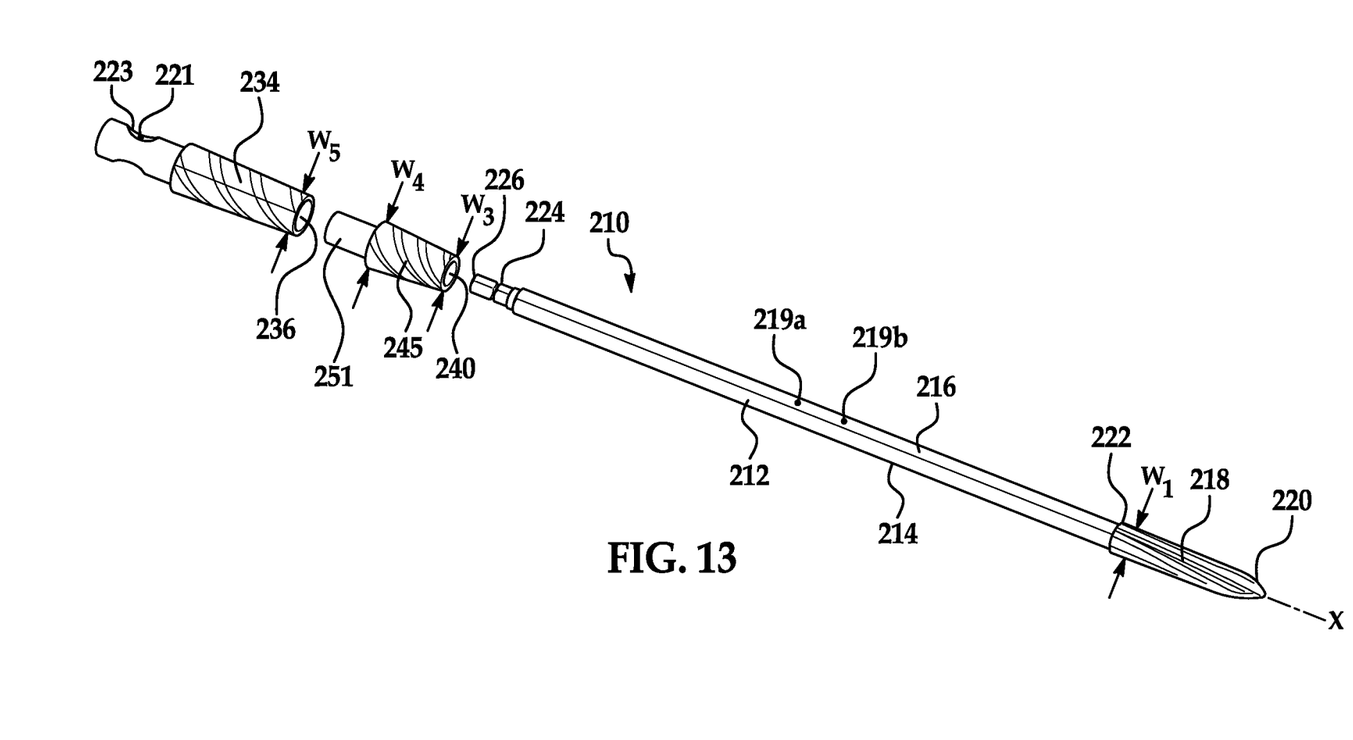
FIG. 13 is an exploded isometric view of a reaming system according to another exemplary embodiment.

Now referring to FIG. 13, another exemplary embodiment of the system 210 is illustrated. Components that correspond to those of FIGS. 1-5 are indicated by corresponding reference numerals, increased by 200.

The system 210 can include a shaft 212 having a first reamer 218 fixed at one end and a drive coupler 224 fixed at an opposite end. The shaft 212 can be substantially similar to the shaft 12 of the embodiments of FIGS. 1 and 2, except the shaft 212 can include at least one detent button 219a, 219b. In some embodiments, the shaft 212 can include a plurality of detent buttons 219a, 219b that are spaced apart along the longitudinal axis X. It will be appreciated that the detent buttons 219a, 219b can be moveable and biased away from the axis X. It will also be appreciated that the shaft 212 can include quick-connect couplings other than the detent buttons 219a, 219b without departing from the scope of the present disclosure.

The system 210 can also include a second reamer 234. The second reamer 234 can be substantially similar to the second reamer 34 of the embodiments of FIGS. 1 and 2, except the second reamer 234 can include an aperture 221. The aperture 221 can receive one of the detent buttons 219a, 219b when positioned on the shaft 212 to fix the second reamer 234 in a longitudinal position on the shaft 212 as will be discussed in greater detail below. The second reamer 234 can also include a recess 223 that surrounds the aperture 221 that provides a comfortable surface for the user to depress the detent button 219a, 219b to remove the second reamer 234 from the shaft 212 as will be discussed in greater detail below.

Furthermore, the system 210 can include a third reamer 245. The third reamer 245 can be tapered so as to have a distal width W3 that is substantially equal to the proximal width W1 of the first reamer 218 and to have a proximal width W4 that is substantially equal to the distal width W5 of the second reamer 234. The third reamer 245 can also include an aperture 240, such as a through hole, that receives the shaft 212. Furthermore, a shaft portion 251 can be fixed on a proximal end of the third reamer 245. The shaft portion 251 can be keyed to the shaft 212 like the embodiments discussed above to inhibit relative rotation of the shaft 212 and third reamer 245. Furthermore, the third reamer 245 can be fluted in the same direction as the first and second reamers 212, 234.

To assemble the system 210, the third reamer 245 can slide longitudinally along the axis X from the proximal end 226 of the shaft 212 toward the first reamer 218. Then, the second reamer 234 can slide longitudinally along the axis X from the proximal end 226 of the shaft 212 toward the first reamer 218 such that the third reamer 245 is disposed between the first and second reamers 218, 234. The aperture 221 of the second reamer 234 can receive one of the detent buttons 219a, 219b to fix the second reamer 234 in an axial position on the shaft 212. The first and second reamer 212, 234 can each abut the third reamer 245 and fix the third reamer 245 in an axial position on the shaft 212 as well. Furthermore, in some embodiments, the third reamer 245 can include an aperture for receiving one of the detent buttons 219a, 219b to fix the third reamer 245 axially.

Then, the first, second, and third reamers 212, 234, 245 can be used to simultaneously form respective pockets within the anatomy of the patient. Like the embodiments discussed above, it will be appreciated that the reamers 212, 234, 245 can be sized according to the prosthesis so that the prosthesis can fit into and fixedly engage the anatomy. Next, to disassemble the system 210, the user presses the detent button 219a, 219b toward the axis X, and the user slides the second and third reamers 234, 245 away from the first reamer 212.

Accordingly, it will be appreciated that the system 210 can be assembled and disassembled quickly and conveniently. Also, it will be appreciated that the third reamer 245 can be optionally used. For instance, the second reamer 234 can be coupled to the shaft 212 independent of the third reamer 245 and fixed in an axial position relative to the shaft 212 by one of the detent buttons 219a, 219b. The detent buttons 219a, 219b can be positioned along the axis X at predetermined intervals according to the geometry of the prosthesis (not shown). Thus, the system 210 can provide substantial versatility.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A method of reaming a femur comprising:
selecting a distal prosthetic member from a plurality of distal prosthetic members;
selecting a proximal prosthetic member from a plurality of proximal prosthetic members;
providing or obtaining a modular reaming system comprising a plurality of distal reamers and a plurality of proximal reamers;
selecting a distal reamer from the plurality of distal reamers based on one or both of a size and geometry of the selected distal prosthetic member to be implanted in the femur;
selecting a proximal reamer from the plurality of proximal reamers based on one or both of a size and geometry of the selected proximal prosthetic member to be implanted in the femur;
removably coupling the selected proximal reamer to a shaft fixed to the selected distal reamer and retaining the selected proximal reamer against rotation relative to the selected distal reamer; and
rotating the shaft in a single direction to substantially simultaneously ream a proximal pocket in the femur with the selected proximal reamer and a distal pocket in the femur with the selected distal reamer.

2. The method of claim 1, wherein removably coupling the selected proximal reamer to the shaft comprises sliding the selected proximal reamer onto the shaft toward the selected distal reamer.

3. The method of claim 2, further comprising retaining the selected proximal reamer in a fixed axial position relative to the shaft.

4. The method of claim 1, further comprising visually indicating a depth of the selected proximal and distal reamers in the femur.

5. A method for reaming a plurality of pockets in an anatomical feature for implanting a distal prosthetic member and a proximal prosthetic member in the anatomical feature, the method comprising:
selecting a distal prosthetic member from a plurality of distal prosthetic members;
selecting a proximal prosthetic member from a plurality of proximal prosthetic members;
selecting a first reamer from a plurality of first reamers based on one or both of a size and a geometry of the selected distal prosthetic member;
selecting a second reamer from a plurality of second reamers based on one or both of a size and a geometry of the selected proximal prosthetic member;
reaming a first pocket in an anatomical feature using the selected first reamer, wherein the selected first reamer reams in a first position on a longitudinal axis; and
reaming a second pocket in the anatomical feature using the selected second reamer, wherein the selected second reamer reams in a second position on the longitudinal axis located proximal to the first position, and the selected first reamer is removably coupled to the selected second reamer;
wherein reaming of the first pocket is substantially simultaneous to reaming the second pocket.

6. The method of claim 5, further comprising forming a reaming assembly by removably coupling the selected first reamer to the selected second reamer with a shaft that is fixedly coupled to the first reamer.

7. The method of claim 6, further comprising contacting a shoulder on the shaft that limits movement of the second selected reamer along the longitudinal axis.

8. The method of claim 6, wherein forming the reaming assembly further includes providing the selected first reamer to have a maximum width that is less than a maximum width of the selected second reamer, disposing the selected first reamer at a distal end of the shaft, and disposing the selected second reamer between the distal end and a proximal end of the shaft.

9. The method of claim 6, further comprising removably fixing the selected second reamer in the second position with at least one biased detent button, wherein the at least one biased detent button is located on the shaft and is removably received by an aperture of the selected second reamer.

10. The method of claim 5, further comprising:
selecting a spacer from a plurality of spacers of various sizes; and
maintaining an amount of space between the selected first reamer and the selected second reamer by disposing the selected spacer between the first reamer and the second reamer.

11. The method of claim 5, further comprising reaming a third pocket using a third reamer that is disposed between the selected first reamer and the selected second reamer at a third position on the longitudinal axis, the third reamer keyed against rotation relative to the selected first reamer to ream the first, second, and third pockets substantially simultaneously.

12. The method of claim 5, further comprising mating a first surface that is fixed relative to the selected first reamer and a corresponding second surface that is fixed relative to the selected second reamer to key the selected second reamer against rotation relative to the first reamer.

13. The method of claim 5, further comprising rotating a drive coupler that is coupled to the selected first and second reamers to drivingly rotate the selected first and second reamers in a same direction about the longitudinal axis to ream the first and second pockets substantially simultaneously while rotating in the same direction.

14. The method of claim 13, wherein the selected first and second reamers are drivingly rotated by a first drive coupler that is fixedly coupled to the selected first reamer and a second drive coupler that is fixedly coupled to the selected second reamer, the selected second reamer receiving the first drive coupler.

15. The method of claim 5, further comprising providing the selected first reamer fluted in a first direction about the longitudinal axis, and the selected second reamer fluted in the first direction about the longitudinal axis to ream the first and second pockets substantially simultaneously.

16. The method of claim 5, further comprising applying a retention member to limit movement of the selected second reamer axially away from the selected first reamer along the longitudinal axis.

17. The method of claim 5, further comprising receiving a first shaft fixed to an end of the selected first reamer by a second shaft fixed to an end of the selected second reamer to removably couple the selected first and second reamers.

18. The method of claim 5, further comprising distally reaming a femur of a patient with the selected first reamer, and simultaneously proximally reaming the femur of the patient with the selected second reamer.

19. A method for reaming a plurality of pockets in an anatomical feature, the method comprising:
providing a reaming assembly comprising a first reamer and a second reamer, the first and second reamers configured to be removably coupled together;
reaming a first pocket in the anatomical feature using the first reamer of the reaming assembly;

implanting a distal prosthetic member into the first pocket in the anatomical feature;

coupling the second reamer to the implanted distal prosthetic member; and reaming a second pocket in the anatomical feature using the second reamer of the reaming assembly, the second pocket located proximal to the first pocket and configured to receive a proximal prosthetic member.

20. The method of claim 19, wherein the reaming assembly further comprises an extension member configured to be removably coupled to the first reamer during reaming of the first pocket.

21. The method of claim 19, wherein the reaming assembly further comprises an alignment rod for use in coupling the second reamer to the implanted distal prosthetic member, such that the second reamer is aligned substantially coaxially relative to the implanted distal prosthetic member.

* * * * *